United States Patent [19]

Labows, Jr. et al.

[11] 4,396,715

[45] Aug. 2, 1983

[54] PRODUCTION OF GAMMA-LACTONE RICH FLAVOR ADDITIVES BY PITYROSPORUM SPECIES CULTURED ON LIPID RICH SUBSTRATES

[75] Inventors: John N. Labows, Jr., Horsham; Guy Webster, Lafayette Hill; Kenneth McGinley, Philadelphia, all of Pa.

[73] Assignee: The Simon Greenberg Foundation, Philadelphia, Pa.

[21] Appl. No.: 205,637

[22] Filed: Nov. 10, 1980

Related U.S. Application Data

[63] Continuation of Ser. No. 26,877, Apr. 4, 1979, abandoned.

[51] Int. Cl.$^3$ ..................... C12P 17/04; C12R 1/645
[52] U.S. Cl. ................................. 435/126; 435/911
[58] Field of Search ................... 435/123, 124, 126

[56] References Cited

PUBLICATIONS

Collins in Lloydia, vol. 39, No. 1, pp. 20-21, (1976).
Journal of Agriculture Food Chem., vol. 24, No. 6, pp. 1247-1249, (1976).
Nature, vol. 194, pp. 995-996, (Jun. 9, 1962).
The Journal of Investigative Dermatology, vol. 64, pp. 401-405, (1975).
Acta Chemica Scandinavica, vol. 19, pp. 370-374, (1965).
The Journal of Investigative Dermatology, vol. 58, No. 3, pp. 155-159, (1972).
Analytical Chemistry, vol. 37, pp. 89-92, (1965).
Journal of the Society of Cosmetic Chemists, vol. XV, pp. 609-626, (1964).
Journal of Institute of Brewing, vol. 83, pp. 32-34, (1977).
Lodder, The Yeasts, pp. 1167-1186, (1970).

*Primary Examiner*—Lionel M. Shapiro
*Attorney, Agent, or Firm*—Woodcock, Washburn, Kurtz, Mackiewicz & Norris

[57] ABSTRACT

Novel odor-flavor materials and methods for producting the same are disclosed comprising a mixture of various gamma-lactones. In the preferred embodiment, a member of the genus Pityrosporum is cultured on a culture medium and is stimulated to produce a gamma-lactone containing flavor-fragrance mixture through its incubation with a lipid rich precursor. The preferred species for use in producing these gamma-lactone containing materials are *P. canis, P. pachydermatis, P. orbiculare* and *P. ovale*. The preferred lipid-rich materials include triolein, sebum, lecithin, oleic acid, and SAB with human sebum, and Tween-80. The resulting gamma-lactone rich products comprise the following lactones: gamma-hexa, gamma-hepta, gamma-octa, gamma-nona, gamma-deca, gamma-undeca, and in the case of *P. canis*, gamma-dodecalactone. The resultant flavor-fragrance product is all natural, exhibiting extremely pleasing taste and/or flavor characteristics.

3 Claims, 1 Drawing Figure

Odor Profile of Pityrosporum ovale

PRODUCTION OF GAMMA-LACTONE RICH FLAVOR ADDITIVES BY PITYROSPORUM SPECIES CULTURED ON LIPID RICH SUBSTRATES This is a continuation of application Ser. No. 026,877, filed Apr. 4, 1979, now abandoned.

BACKGROUND OF THE INVENTION

It has long been desired to impart pleasant flavors and/or odors to various substrates particularly, as flavorings in food and fragrances in perfumes. Over the years, particular fragrances and/or flavors have been identified with certain chemical compounds. It is known, for example, that various gamma-lactones possess desirable odor/flavor characteristics. As reported in *Fernaroli's Handbook of Flavor Ingredients,* Volume II, 2nd edition, CRC Press, 1975, gamma-hexalactone is known to possess the flavor-fragrance characteristics of coumarin or carmel. Gamma-heptalactone is known to have a caramel or nutty odor and flavor, while gamma-octalactone is known to exhibit the flavor-fragrance of coconut or tonka. Gamma-nonalactone has a cream, coconut or fruity odor/flavor characteristic, while gamma-decalactone's flavor-fragrance is creamy peach or apricot. A peach or apricot odor/flavor is also exhibited by gamma-undecalactone, while a buttery or peach odor/flavor is exhibited by gamma-dodecalactone.

In addition to the above-mentioned lactones, various alcohols and many other compounds are known to exhibit identifiable odor/flavors. For example, phenyl ethanol is known to exhibit a rose/peach flavor-fragrance while benzyl alcohol is known to exhibit a fruity odor/flavor.

Although each of the above-mentioned compounds are known to be flavor-fragrance additives, their manufacture to date has normally been effected by artificial means. More recently, however, artificial flavor and/or fragrance additives have become increasing suspect and are now generally less preferred over those food additives which are naturally derived. Additionally, depending upon the particular artificial or synthetic process utilized in manufacturing particular flavorants, various artificial contaminants may be contained in the final product, which contaminants may exhibit undesirable side effects which would dictate against their routine use in flavor-fragrance materials.

It has also been observed that one or more species of yeast or bacteria, when cultured under certain specific conditions, exhibit odors. For example, lactones have been reported as metabolites of various microorganisms, such as the soil fungus *Trichoderma viride* which is known to produce a delta-lactone, 6-pentyl-2-pyrone, as its major odorant. See Collins, R. P., 1976, "Terpenes and Odoriferous Materials from Microorganisms", Lloydia 39: 20. Another organism, *Ceratocystis moniliformis,* generates gamma-decalactone when glycerol is used as a major substrate. See Lanza, E., K. H. Ko, and J. K. Palmer, 1976, "Aroma Production by Cultures of *Ceratocystis moniliformis*", Journal of Agriculture Food Chem. 24: 1247. Microorganisms are also known which can reduce gamma-keto-acids to gamma-hydroxy-acids which then cyclize to gamma-lactones. See Muys, G. T., B. van der Ven, and A. P. de Jonge, 1962, "Synthesis of Optically Active Gamma and Delta-Lactones by Microbiological Reduction", Nature 194: 955. As mentioned in the Collins article referred to above, phenyl ethanol and pentanol have also been reported as being formed by various microorganisms.

Of course, many bacterial and/or yeast species are known to exist which do not produce any substantial volatile by-products, much less any gamma-lactones. The genus Pityrosporum is known to comprise four species, *P. ovale, P. orbiculare, P. canis,* and *P. pachydermatis.* See Lodder, J., 1971, "The Yeasts", North-Holland Publishing Co., Amsterdam, *P. ovale* and *P. orbiculare* are known to occur in areas rich in sebaceous glands, such as the scalp, face and trunk, *P. ovale,* being the most numerous organism on the scalp. See McGinley, K. J., J. J. Leyden, R. R. Marples, and A. M. Kligman, 1975, "Quantitative Microbiology of the Scalp in Non-Dandruff, Dandruff, and Seborrheic Dermatitis", Journal of Investigative Dermatology, 64: 401. Despite being ubiquitous, members of this genus are ill-defined, and morphologic characteristics serve as the prime method of identification (see the Lodder article referred to above).

Occasionally, mostly in anecdotal references in the scientific literature, various types of bacteria and/or yeast cultures are described as emitting perceptible odors. In one such instance, a culture containing *P. ovale* with Sabouraud's agar overlayed with olive oil was described as emitting a "distinctive, fruity, odor" Van Abbe, N. J., (1964) "The Investigation of Dandruff", *Journal of the Society of Cosmetic Chemists,* Vol. XV, p.609. Of course, without identifying the particular chemical constituent(s) which might cause of such odor and/or without further identifying whether and which of the experimental conditions may have led to the perception of such odor, such anecdotal references are of little use to the flavor-fragrance industry in its quest for new and improved flavor-fragrance additives.

SUMMARY OF THE INVENTION

The present invention provides a new method of manufacturing a novel odoriferous flavoring product comprising a mixture of gamma-lactones. The product of this new method exhibits an extremely pleasing odor/flavor which, due to its all natural origins, should be particularly useful to the flavor-fragrance industry.

The method of the present invention comprises culturing a member of the yeast genus Pityrosporum on or in a culture medium while using a lipid rich precursor-stimulant to produce a novel flavor or fragrance product which comprises a mixture of gamma-lactones. This lipid rich precursor may be included in or added to the basic culture medium and should provide sources of fatty acid as well as glycerol. When *P. ovale, P. pachydermatis* or *P. orbiculare* are the organisms selected for incubation, the resulting product comprises gamma-hexalactone, gamma-heptalactone, gamma-octalactone, gamma-nonalactone, gamma-decalactone, and gamma-undecalatone. When *P. canis* is used as the species for incubation, the mixture additionally comprises gamma-dodecalactone. Phenyl ethanol, benzyl alcohol, hexanol and pentanol are also present in these products, the latter two of which are not believed to substantially contribute to the odor or flavor characteristics of the product.

In the preferred embodiment, a culture medium, preferably a solid medium, is employed such as Sabouraud-dextrose, which when combined with a lipid rich substrate not only encourages growth of the preselected Pityrosporum species, but also results in a marked increase in lactone-product production. The preferred culturing media include Littman agar (which also contains a liid source), Sabouraud-dextrose agar (SAB) with 1% Tween-80 (Baltimore Biological Laboratory, BBL), and Yeast Nitrogen Base with 1.5% agar (YNBA). The preferred precursor-stimulants include the following: L-alpha-lecithin, oleic acid, triolein, human sebum and/or Sabouraud-dextrose agar with human sebum all of which provide a source of Triglycerides. All Pityrosporum cultures produce gamma-octa, gamma-nona, and gamma-decalactones, with gamma-decalactone normally being the major lactone component. Experimental procedures including suitable controls indicate that these lipid rich substrates, when introduced in combination with a suitable culture medium, are converted by the Pityrosporum species to produce the desired gamma-lactone end product mixture. Accordingly, Pityrosporum may be employed to provide a simple and inexpensive method of producing a pleasing flavor mixture of gamma-lactones which may be used to impart their characteristic fragrance to perfumes and flavors to foods.

DETAILED DESCRIPTION OF THE INVENTION

Figure 1:
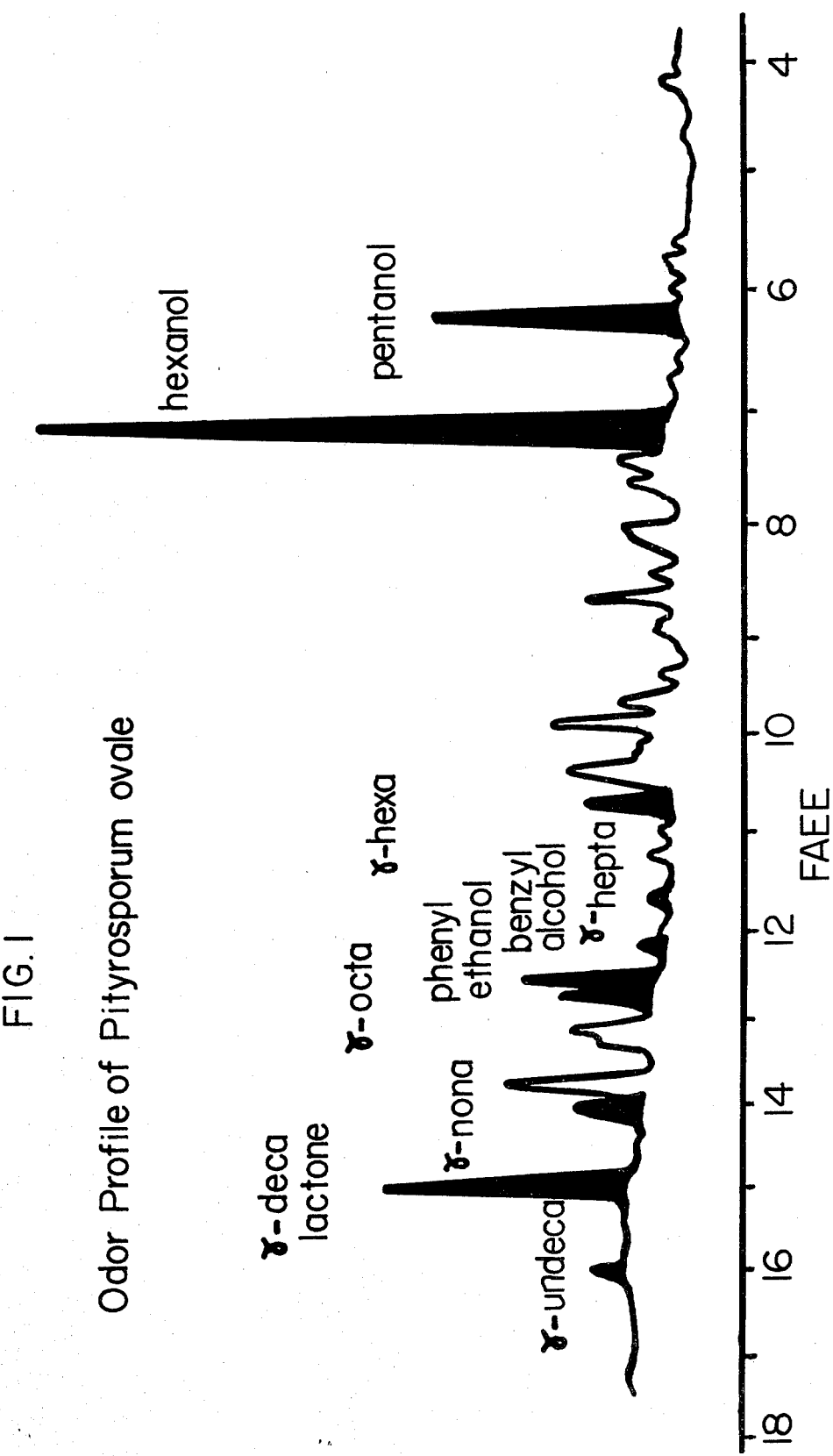
FIG. 1 is an odor profile of P. ovale showing the FAEE values for various gamma-lactones, phenyl ethanol, benzyl alcohol, hexanol and pentanol.

In accordance with the procedures set forth hereinafter, volatiles produced by the genus Pityrosporum and other yeast genera were collected and concentrated from the head space above the culture. Gas chromatography-mass spectometry (GC/MS) was employed for separation and structure elucidation of the volatiles. The particular microorganisms employed were P. ovale strains American Type Culture Collection (ATCC) #24047, 12078, 14521; P. pachydermatis ATCC #24022; P. canis ATCC #14522; P. obiculare ISG 6331 (obtained from Dr. M. Nazarro-Porro, Institute of Dermatology, St. Gallicano Rome, Italy), Candida albicans, Saccharomyces cereviciae, Rhodotorula rubrum, and Torulopsis galabrata (Duhring culture collection). Each of these strains were cultured on Littman agar and Sabouraud-dextrose agar (SAB) (Baltimore Biological Laboratory, BBL) with 1% Tween-80 (Atlas Chemical) and incubated for 37° for 7 days in culture flasks sealed with cotton plugs. P. ovale was cultured on Yeast Nitrogen Base (BBL) with 1.5% agar (YNBA) supplemented by the following: L-alpha-lecithin (1%) (Sigma Chemical), oleic acid or triolein (1%) (Sigma Chemical), human sebum (1%) collected by the method of Marples et al (see Marples, R. R., D. T. Downing, and A. M. Kligman, 1972, "Influence of Pityrosporum Species in the Generation of Free Fatty Acids in Human Surface Lipids", Journal of Investigative Dermatology, 58: 155) and SAB with human sebum (1%).

Preliminary studies have indicated that a higher recovery of volatiles was obtained when a solid rather than a liquid culture medium was used. It is believed that this may relate to the entrapment of volatiles in the liquid phase, and accordingly the following reported experiments have employed solid media.

The above-mentioned culture flasks were 250 ml single or double neck round-bottom flasks. Prior to sampling, the flasks were fitted with a nitrogen inlet tube and an outlet tube which was attached to a 6 inch by $\frac{1}{8}$ inch stainless steel tube containing 70 mg of Tenax (Applied Science), an organic polymeric absorbent. The headspace of the culture was swept with nitrogen at a flow rate of 90 ml per minute for 17 hours at 37°. The collected volatiles were then backflushed with heating (220° for 10 minutes) onto the front 15 cm of the gas chromatographic (GC) column which was cooled with dry ice. The volatiles were then separated and identified by combined gas chromatographic-mass spectrometric (GC/MS) analyses. The GC column was a 10 foot by 2 mm pyrex 20 M Carbowax on Gas Chrom Q programmed at 70° (4 minutes), 70°–220° (4°/minutes). The GC/MS system was a Perkin-Elmer 990 GC interfaced with a Watson-Biemann separator to a Hitachi/Perkin-Elmer RMU-6L Mass Sepctrometer (see Watson, J. T. and K. Biemann, 1965, "Direct Recording of High Resolution Mass Spectra of Gas Chromatographic Effluents", Anal. Chem. 37: 844). Individual components were identified by comparison of their Fatty Acid Ethyl Ester(FAEE) retention indices on a Carbowax column with those previously reported (see van den Dool, H. and P. D. Kratz, 1963, "A Generalization of the Retention Index System Including Linear Programmed Gas-Liquid Partition Chromatography", Journal of Chromatography 11: 463; Withycombe, D., R. Lindsay, and D. Stuiber, 1978, "Isolation and Identification of Volatile Components from Wild Rice Grain", Journal of Agriculture Food Chemistry, 26: 816). Individual components were also identified by comparison of retention time and mass spectral data with authentic samples, or by reported mass spectral data (see Honkanen, E., T. Moisio, and P. Karvonen, 1965, "The Mass Spectra of Some Aliphatic Lactones", Acta Chem. Scand. 19: 370; McFadden, W., E. Day, and M. Diamond, 1965, "Correlations and Anomalies in Mass Spectra Lactones", Anal. Chem. 37: 89). FAEE values obtained for the gamma—lactones include: gamma-hexa, 10.6; gamma-hepta, 11.7; gamma-octa, 12.6; gamma-nona, 14.0; gamma-deca, 15.0; gamma-undeca, 16.1; gamma-dodeca, 17.4. Uninoculated culture media, sterilized either by autoclaving or by millipore filtration, showed several volatile components including alkyl pyrazines, phenol, benzaldehyde, acetophenone, and furfural. Either olfactory or mass spectral analysis was necessary to confirm the presence of the lactones in cultures containing triolein because of the interfering contaminants in the triolein itself, some of which appear to be alkyl phenols. Blank SAB cultures also contained trace amounts of pentanol and phenylethanol.

The odor-profile obtained for P. ovale on Lecithin-/YNBA is shown in FIG. 1. The major odorants include a homologous series of gamma-lactones. The presence of the gamma-lactones was readily confirmed by mass spectral analysis since they undergo side chain cleavage to give an intense base peak at m/z 85 (see the Honkanen, et al article referred to above). Increased sensitivity for detection of gamma-lactones which were present in trace amounts was obtained by selective single ion monitoring of the GC effluent at this mass. All Pityrosporum cultures showed octa-, nona-, and gamma-decalactones with gamma-decalactone normally being the major lactone component. See Table I:

TABLE I

ODOR PROFILE OF PITYROSPORUM GENUS

| | Species | | | | | | | |
|---|---|---|---|---|---|---|---|---|
| | P. ovale | | P. orbiculare | | P. canis | | P. pachydermatis | |
| Compounds* | a | b | a | b | a | b | a | b |
| γ-octalactone | 30 | ** | 7 | 10 | 6 | 0 | 2.5 | ** |
| γ-nonalactone | 7 | 1 | 3 | 6 | 5 | 0 | 1 | 1 |
| γ-decalactone | 21 | 15 | 33 | 48 | 28 | 18 | 7 | 10 |
| γ-undecalactone | 0 | 0 | 0 | 0 | 2 | 0 | 0 | 0 |
| γ-dodecalactone | 0 | 3 | 19 | 0 | 5 | 0 | 0 | 3 |
| pentanol | 60 | 4480 | 88 | 252 | 0 | 1728 | 65 | 1000 |
| hexanol | 200 | 4 | 6 | 0 | 0 | 0 | 18 | 6 |
| benzyl alcohol | 14 | 6 | 7 | 16 | 50 | 20 | 100 | 6 |
| 2-phenylethanol | 26 | 2240 | 0 | 80 | 46 | 1288 | 29 | 1000 |

Key: a = cultured on Littmann agar
b = cultured on SAB-dextrose with 1% Tween
*Values are relative peak intensities on $2 \times 10^{-9}$ amps with ½ material going to the mass spectrometer.
**Overlap of peak with phenylethanol peak Olfactory analysis of culture plates of Pityrosporum indicated an odor very similar to that of the gamma-decalactone. Phenylethanol and gamma-octalactone have similar retention times and in most cases the lactone appears as a shoulder on the larger phenylethanol peak. In some cultures, gamma-undecalactone and gamma-dodecalactone were also observed.

The volatiles which could be identified from the analysis of culture headspaces of S. cereviciae, Rh. rubrum, T. galabrata, and C. albicans on both SAB with Tween-80 and on Littman agar are shown in Table II:

TABLE II

ODOR PROFILE OF OTHER YEAST GENERA

| | Rh. rubrum | | C. albicans | | T. gaiabrata | | S. cereviciae | |
|---|---|---|---|---|---|---|---|---|
| Compounds* | a | b | a | b | a | b | a | b |
| lactones | 0 | 0 | 0 | 0 | 0 | 0 | 0 | 0 |
| pentanol | 36 | 8896 | 45 | 95 | 215 | 426 | 172 | 3936 |
| hexanol | 0 | 90 | 0 | 0 | 0 | 0 | 0 | 0 |
| benzyl alcohol | 0 | 0 | 3 | 0 | 0 | 0 | 0 | 0 |
| 2-phenylethanol | | ** | 192 | 364 | 4000 | 156 | 704 | 572 | 269 |

Key: a = cultured on Littmann agar
b = cultured on Sabouraud-dextrose with 1% Tween
*Values are relative peak intensities on $2 \times 10^{-9}$ amps with ½ the material going to the mass spectrometer.
**Overlap of peak with culture contaminants The strains tested all failed to produce detectable amounts of gamma-lactones. In all cultures on SAB with 1% Tween-80, phenylethanol and pentanol were present in large amounts. Minor components in the cultures are being analyzed to determine if there are distinguishing features in each of the headspace analyses which might be distinctive of each microorganism. For example, S. cereviciae on SAB with Tween-80 shows the presence of ethyl octanoate and trace amounts of ethyl decanoate.

In additional experiments, P. ovale (the most common yeast found on the human skin) was cultured on YNBA with individually added substrates in order to assess the requirements for gamma-lactone formation. No growth was observed on YNBA with added glycerol. The addition of lecithin resulted in the production of six different gamma-lactones including gamma-hexalactone and gamma-heptalactone which were not seen on the other culture media (FIG. 1 and Table III). With added oleic acid, triolein, or human sebum, gamma-lactones are also produced (Table III):

TABLE III

ODOR PROFILE OF P. OVALE ON SELECTED MEDIA

| | Substrates | | | |
|---|---|---|---|---|
| Compounds* | YNBA/Lecithin | YNBA/Oleic Acid[a] | YNBA/Sebum | SAB/Sebum[b] |
| γ-hexalactone | 15 | 0 | 0 | 0 |
| γ-heptalactone | 3 | 0 | 0 | 0 |
| γ-octalactone | 20 | 3 | 11 | ** |
| γ-nonalactone | 15 | 3 | 8 | 180 |
| γ-decalactone | 42 | ** | 0 | 340 |
| γ-undecalactone | 8 | 0 | 0 | 33 |
| γ-dodecalactone | 0 | 0 | 0 | ** |
| pentanol | 45 | 80 | 0 | 210 |
| hexanol | 280 | 70 | 0 | 0 |
| benzyl alcohol | 4 | 0 | 10 | 120 |
| 2-phenylethanol | 24 | 0 | ** | 5760 |

Key: [a] many additional peaks from oleic acid itself
[b] 14 day culture; 34 hour collection
*Values are relative peak intensities on $2 \times 10^{-9}$ amps with ½ the material going to the mass spectrometer.
**Overlap of peak with other components The gas chromatographic profiles of P. ovale on YNBA or SAB media with added sebum are complicated by additional peaks from sebum itself, such as the food antioxidants butylated-hydroxytoluene and ditertiarybutyl-hydroxyanisole. See Labows, J., G. Preti, E. Hoelzle, J. Leyden, and A. Kligman, in press, "Analysis of Human Axillary Volatiles: Compounds of Exogenous Origin". Slightly longer incubation time results in a scalp-like odor in these cultures. In spite of this problem, headspace analysis shows the presence of short-chain aliphatic acids, gamma-lactones and other unidentified components.

As seen from the above, yeasts of the genus Pityrosporum, when incubated on selected media containing lipid rich precursor—stimulants, emit a unique odor-profile exhibited by a homologus series of gamma-lactones. These lactones have been identified by gas chromatography-mass spectometry analysis of culture headspace. Since other commonly identified yeasts species cultured on lipid-containing media do not give off lactones, this characteristic profile may additionally be used to identify and distinguish Pityrosporum from other yeast genera. Additionally, the readily recognizable "canned-peach" fruity odor of this homologous series of gamma-lactones make the products of these cultures extremely valuable as flavor—fragrance materials.

The above-mentioned in vitro studies clearly demonstrate that a source of lipid is essential for both P. ovale growth and lactone production. It is speculated that human sebum provides sufficient nutrients for P. ovale growth in vivo, however, when P. ovale is added in vitro to a medium such as Sabouraud-dextrose with added human sebum, a marked increase in gamma-lactone production occurs. While the precise metabolic pathway for lactone production is uncertain, it is presently believed that P. ovale may possess a lipase system which can hydrolyze triglycerides to glycerol and free fatty acids, either of which, but probably glycerol, can be used to form lactones. See Marples, et al as referred to above.

The preferred embodiment product of the present invention also may comprise phenylethanol and pentanol, and in some case also additional compounds chemically related to phenylethanol, such as styrene, phenyl acetaldehyde, and phenylethanol acetate.

As seen from the above, a simple and inexpensive method of providing a novel gamma-lactone containing flavor-fragrance product is described wherein one or more species of the genus Pityrosporum are cultured on a medium containing additions of lipid-rich stimulant-precursors. The result is a novel flavor-fragrance material which is derived from entirely natural origins.

It will be understood that various changes in the details, materials and arrangement of parts which have been herein described and illustrated in order to explain the nature of this invention may be made by those skilled in the art within the principle and scope of the invention as expressed in the following claims.

It will further be understood that the "Abstract of the Disclosure" set forth above is intended to provide a non-legal technical statement of the contents of the disclosure in compliance with the Rules of Practice of the United States Patent and Trademark Office, and is not intended to limit the scope of the invention described and claimed herein.

What is claimed is:

1. A method of making a flavor-fragrance product having a gamma-lactone component comprising octa-, nona- and deca-lactones, which product is substantially free of gamma-undecalactone, comprising the steps of:
   (a) providing a substantially sterile Littman agar culture medium;
   (b) combining with said culture medium lipid rich precursor-stimulant means for stimulating production of gamma-lactone flavor-fragrance products during succeeding incubation; and
   (c) incubating said medium combined with said lipid rich precursor-stimulant means with a biologically active inoculant consisting essentially of at least one member of the genus Pityrosporum, said member being P. ovale.

2. A method of making flavor-fragrance product having a gamma-lactone component comprising nona- and deca-lactones, which product is substantially free of gamma-undecalactone, comprising the steps of:
   (a) providing a substantially sterile SAB-dextrose containing Tween;
   (b) combining with said culture medium lipid rich precursor-stimulant means for stimulating production of gamma-lactone flavor-fragrance products during succeeding incubation; and
   (c) incubating said medium combined with said lipid rich precursor-stimulant means with a biologically active inoculant consisting essentially of at least one member of the genus Pityrosporum, said member being P. ovale.

3. A method of making a flavor-fragrance product having a gamma-lactone component comprising octa- and nona-lactones, which product is substantially free of gamma-undecalactone, comprising the steps of:
   (a) providing a substantially sterile yeast nitrogen base and agar culture medium;
   (b) combining with said culture medium a lipid rich precursor-stimulant means for stimulating production of gamma-lactone flavor-fragrance products during succeeding incubation, said precursor-stimulant means being oleic acid; and
   (c) incubating said medium combined with said lipid rich precursor-stimulant means with a biologically active inoculant consisting essentially of at least one member of the genus Pityrosporum, said member being P. ovale.

* * * * *